(12) United States Patent
Bencini

(10) Patent No.: US 11,033,417 B2
(45) Date of Patent: Jun. 15, 2021

(54) PROSTHESIS FOR ENTEROSTOMY PATIENTS

(71) Applicant: Claudio Bencini, Fauglia (IT)

(72) Inventor: Claudio Bencini, Fauglia (IT)

(*) Notice: Subject to any disclaimer, the term of this patent is extended or adjusted under 35 U.S.C. 154(b) by 309 days.

(21) Appl. No.: 15/779,069

(22) PCT Filed: Nov. 25, 2016

(86) PCT No.: PCT/IB2016/057122
§ 371 (c)(1),
(2) Date: May 24, 2018

(87) PCT Pub. No.: WO2017/089994
PCT Pub. Date: Jun. 1, 2017

(65) Prior Publication Data
US 2018/0353319 A1    Dec. 13, 2018

(30) Foreign Application Priority Data
Nov. 26, 2015   (IT) ........................ UB2015A005928

(51) Int. Cl.
*A61F 5/441*    (2006.01)
*A61F 5/44*    (2006.01)
(Continued)

(52) U.S. Cl.
CPC .......... *A61F 5/4407* (2013.01); *A61F 5/0093* (2013.01); *A61F 5/441* (2013.01);
(Continued)

(58) Field of Classification Search
CPC ............ A61F 2005/4455; A61F 5/4405; A61F 5/4407; A61F 5/441; A61F 5/445
See application file for complete search history.

(56) References Cited

U.S. PATENT DOCUMENTS

| 6,485,476 B1 | 11/2002 | Von Dyck et al. |
| 2011/0306823 A1 | 12/2011 | Göbel et al. |
| 2013/0197458 A1 | 8/2013 | Salama |

FOREIGN PATENT DOCUMENTS

| DE | 2431888 A1 | 1/1976 |
| IT | 1198697 B | 12/1988 |

OTHER PUBLICATIONS

WIPO, European International Search Authority (Rijswijk, NL), International Search Report and Written Opinion dated Feb. 8, 2017 in International Patent Application No. PCT/IB2016/057122, 9 pages.

*Primary Examiner* — Christine H Matthews
(74) *Attorney, Agent, or Firm* — Masuvalley & Partners

(57) ABSTRACT

The prosthesis for enterostomy patients comprises: a tubular element of elongated shape and insertable substantially to size inside of a stoma made on the abdominal wall of a patient; a first obstruction means to obstruct at least one area of the stoma, associated with a first end of the tubular element and movable between a restricted configuration and an enlarged configuration to allow the insertion/extraction into/from the stoma respectively, and to prevent leakage of feces from the stoma itself; a first through duct made on the tubular element, communicating with the first obstruction balloon and having valve connectable to a forced introduction/extraction disposable syringe for conduction of a fluid into/from the first obstruction balloon; a second through duct made on the tubular element, communicating with the inside of the stoma and having an active carbon filter for the outflow of gases from the stoma itself; and an external retaining element associated with a second end of the tubular element opposite to the first end and able to cooperate with at least one portion of the abdominal wall and having at least two through holes arranged at the first duct and the second duct; in which at least one of the tubular element and the (Continued)

retaining element is made at least partially of a flexible material.

10 Claims, 4 Drawing Sheets

(51) Int. Cl.
*A61F 5/445* (2006.01)
*A61F 5/00* (2006.01)
(52) U.S. Cl.
CPC ............ *A61F 5/445* (2013.01); *A61F 5/4405* (2013.01); *A61F 2005/4455* (2013.01)

PROSTHESIS FOR ENTEROSTOMY PATIENTS

RELATED APPLICATIONS

This application is the U.S. National Phase of and claims priority to International Patent Application No. PCT/162016/057122, International Filing Date Nov. 25, 2016, entitled Prosthesis For Enterostomy Patients; which claims benefit of Italian Application No. UB2015A005928 filed Nov. 26, 2015 entitled Protesi Per Enterostomizzati; both of which are incorporated herein by reference in their entireties.

TECHNICAL FIELD

The present invention relates to a prosthesis for enterostomy patients.

BACKGROUND ART

In medical practice, as a result of severe intestinal diseases or to complete surgery, amputation of the terminal stretch of the bowels may result necessary, which must be put into connection with the outside in order to be able to discharge the contents thereof.

For this purpose it is common practice to make an enterostomy, i.e. a practice intended to constitute a "stoma", i.e. a praeternatural opening made in the abdominal wall and intended to connect any point of the intestine with the outside, in such a way as to allow the discharge of intestinal contents, i.e. feces and gases. As a result of the amputation of the terminal stretch of the bowels, voluntary continence control is lacking, necessitating the discharge to the outside of the intestinal contents.

To solve these problems bags are used today, among enterostomy patients, applicable directly to the stoma and suitable for the collection of feces freely spilled outside.

These bags, however, have several drawbacks that hinder the patient's normal social reintegration, seriously jeopardizing the patient's quality of life.

In fact, in addition to creating aesthetic problems, the use of such bags, not providing for the recovery of voluntary evacuation control, involves a complex and frequent maintenance, to be repeated at short time intervals and also several times a day, forcing the patient to stay close to toilets.

Furthermore, the use of such bags is not free from possible complications related to the presence of bonding agents which enable it to adhere to the patient's skin.

Added to this is the fact that these bags require frequent changes, resulting in a high expenditure of time in the change of the used bags and difficulties in the disposal of the same by the patient.

Furthermore, it is easy to understand how the need for frequent changes involves not negligible replacement costs of the used bags.

However, to overcome at least partly the above mentioned drawbacks, artificial occluding prostheses have been developed. This type of prosthesis is useful to ensure the voluntary continence control by means of the reversible occlusion of the stoma.

In detail, such occlusion must be partial in such a way as to prevent the outflow of feces and, at the same time, allow the gases to escape.

The use of the above artificial prostheses, which does not exclude their alternation with the containment bags, is undertaken during the terminal stage of the stoma cicatrization that, up to that time, provides for the use of known bags.

A first type of the above artificial prosthesis consists of two or more separate parts which interact with each other by simple electromagnetic attraction.

In detail, these artificial prostheses comprise a support element of substantially annular conformation and magnetized, which is surgically implanted in the abdominal subcutaneous tissue of the patient, at the loop concerned by the stoma, and a closure element having a metal perimeter band which provides for the occlusion of the stoma associating with the annular element by electromagnetic attraction.

Nevertheless, the implantation of the above artificial prostheses requires for complex surgery having many possible complications such as infections of the peristomal tissue, as well as the need for periodical irrigation intended to keep the bowels cleaned over time.

A second type of artificial prosthesis, based on the same principle of electromagnetic attraction between the parts constituting the prosthesis itself, involves the bonding operation on the skin surrounding the stoma of an interchangeable ring on which a magnetized closure element is made to adhere. Even this second type of artificial prosthesis has however some drawbacks related to the presence of adhesive substances which, as a result of prolonged contact with the skin, often cause irritation.

Added to this is the need to provide for frequent irrigations of the bowels, so that the latter remains empty; it is easy to understand that the aforementioned types of prostheses are not very appealing to patients, greatly increasing the discomfort linked to a clinical condition already complex in itself.

Besides these types of prostheses there are others that provide for the bonding of the ring to the skin and the association by interlocking to the closure element; also in this case, however, repeated and frequent irrigations of the bowels are necessary, increasing the discomfort on the part of patients involved in these situations.

Because of the above drawbacks and discomforts for patients, these prostheses are much less common today.

In view of these problems, starting from about 1980, artificial prostheses have been developed consisting of a single monolithic body and made of a rigid and non-deformable material. These prostheses comprise a tubular element insertable inside of the stoma and associated at one end with external retaining means adapted to cooperate with the patient's body.

In detail, such retaining means are made in the form of a flange element adapted to abut against the patient's skin.

The tubular element has locking means comprising a balloon that, when inflating, allows the locking of the tubular element inside of the stoma and, when deflating, permits the insertion and extraction thereof.

Such prostheses however, being made of a rigid material, are rather annoying during the flexion movements of the torso, or for example with a prolonged time in the sitting position.

To obviate at least in part the aforesaid drawbacks prostheses have been developed comprising a tubular element having a deformable body at the end inserted inside of the stoma, that is, opposite to the external retaining means.

To date, a further type of prosthesis has been manufactured, comprising a tubular element associated at one end with a flange element adapted to cooperate with the body of a patient. The tubular element has, furthermore, an expandable locking element adapted to retain the tubular element itself inside of the stoma and substantially shaped as a catheter; in other words, the tubular element has thin walls and a large inner cavity which is used for the emptying irrigations of the intestinal contents while the tubular element is positioned in place, connected to a collection bag. The realization of this type of prosthesis has been provided both in a rigid and in a soft material.

The solution made of a soft material is used in severe cases of bedridden patients, the use has been tested by maintaining the prosthesis in place inside of the stoma for long periods in order to facilitate the maintenance of the ostomy by the assigned personnel, and also to prevent and possibly treat serious injuries of the peristomal or perianal tissues in non self-sufficient patients or patients in a coma.

This type of prosthesis has not been widely used, and a more advanced model has been created, similar to a catheter aimed at the diversion of the intestinal contents away from the skin surface intended to avoid the contact of the intestinal contents in case of serious diseases such as burns, ulcers, infections of the area surrounding the ostomy.

Such models of prosthesis are also used in non self-sufficient and bedridden patients to facilitate the treatment of the ostomy by the assigned personnel.

To overcome these drawbacks another type of prosthesis has been set up having a cylinder in dehydrated hydrophilic material and surrounded by a water-soluble and impermeable film that dissolves in contact with intestinal fluids, resulting in the inflation of the balloon that takes on a substantially truncated cone conformation.

The aforesaid conformation does not ensure the sealing and locking of the prosthesis inside of the stoma, so the adhesion of the outer flange to the skin must be ensured by means of a glue completely similar to that of the collection bags, in order to avoid the exit of the prosthesis itself.

A final type of known prosthesis consists of a single monolithic body having a hollow tubular element made of a rigid material having a first end associated with a flange element and a second end associated with a balloon which, when filled with a fluid, dilates beyond the abdominal wall, locking the prosthesis itself inside of the stoma.

The continence of feces and gases is obtained by inflating the balloon, while the outflow of the feces is performed, without deflating the balloon at the end of the device, by means of the total deflation of the balloon inside of the hollow stem; in detail, the collection of the feces takes place through the association of a containment bag with the flange element, or through irrigation by means of a suitable integrated system.

In parallel, the outflow of the gases takes place by means of partial deflation of the balloon inside of the stem.

This type of prosthesis is also described in patent documents DE2431888, U.S. Pat. No. 6,485,476, US2011/306823 and US2013/197458.

Said prosthesis is anchorable inside of the stoma for a time no longer than 28 days, time beyond which the prosthesis must be replaced.

It is easy to understand how the use of such prosthesis of known type proves complex and cumbersome, to which the fact is added that it requires a complex kit of integrated parts.

DESCRIPTION OF THE INVENTION

The main aim of the present invention is to devise a prosthesis for enterostomy patients adaptable to the positions taken by the patient without causing discomfort and inconvenience, allowing for maximum freedom of movement and increasing, compared to the devices of known type, comfort and convenience of use.

Another object of the present invention is to devise a prosthesis for enterostomy patients which greatly increases the quality of life of enterostomy patients. Another object of the present invention is to devise a prosthesis for enterostomy patients which allows to control the outflow of the intestinal contents thus allowing patients to use commonly widespread toilets, including the toilets in the means of transport without the need to dispose of collection bags full of intestinal contents with their own means.

A further object of the present invention is to devise a prosthesis for enterostomy patients which eliminates the inconvenience linked to the need to perform periodic cleaning procedures of the intestinal contents by means of the complex and costly practice of irrigation.

Another object of the present invention is to devise a prosthesis which allows overcoming the mentioned drawbacks of the prior art within the ambit of a simple, rational, easy, effective to use and affordable solution.

The above mentioned objects are achieved by the present prosthesis for enterostomy patients having the characteristics of claim 1.

BRIEF DESCRIPTION OF THE DRAWINGS

Other characteristics and advantages of the present invention will become better evident from the description of a preferred, but not exclusive, embodiment of a prosthesis for enterostomy patients, illustrated by way of an indicative, but non-limiting, example in the accompanying drawings, wherein.

EMBODIMENTS OF THE INVENTION

Figure 1:
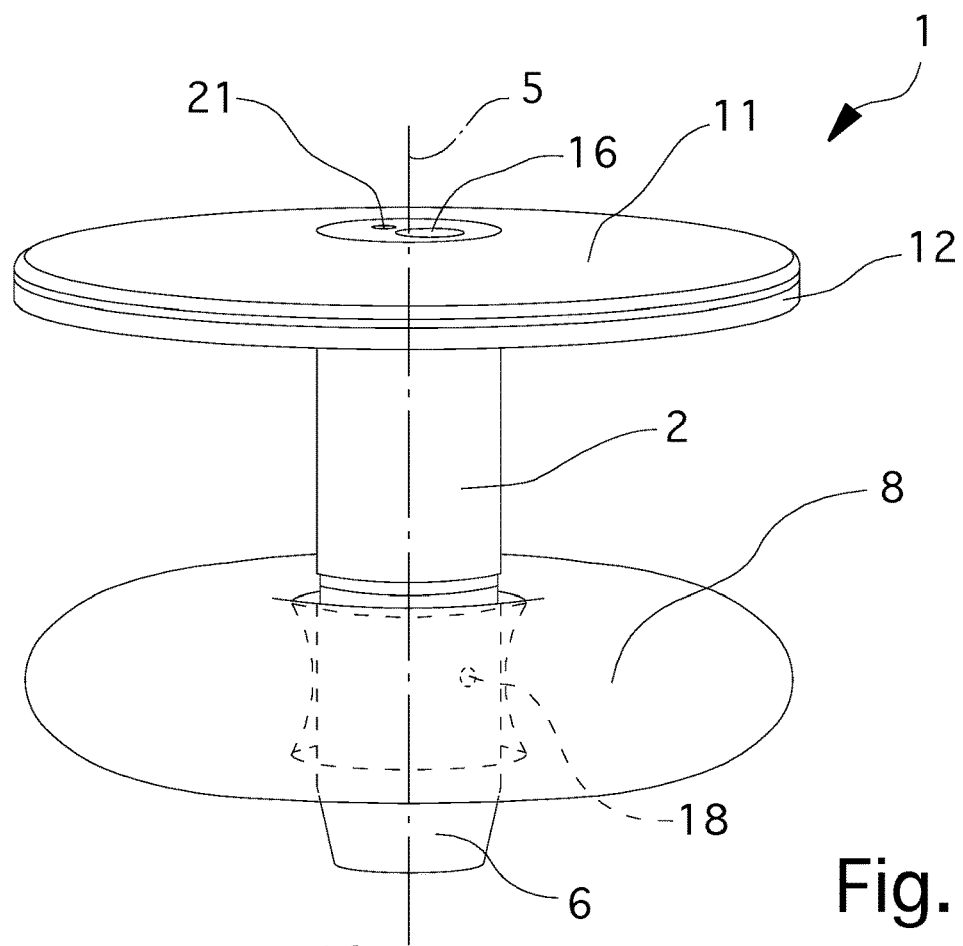
FIG. 1 is a front view of the prosthesis according to the invention in a first embodiment.

With particular reference to such figures, globally indicated with reference number 1 is a prosthesis for enterostomy patients.

The prosthesis 1 comprises a tubular element 2 of elongated shape and insertable substantially to size inside of a stoma 3 made on the abdominal wall 4 of a patient.

With reference to the particular embodiment shown in the figures, the tubular element 2 is coaxial to a longitudinal axis 5 and has a first end 6 insertable inside of the stoma 3, and a second end 7 intended to stay outside of the stoma itself.

The tubular element 2 has a diameter substantially mating to the diameter of the stoma 3 so as to be inserted to size or with a slight play inside of the same, and a greater length than the thickness of the abdominal wall 4 so that once inserted it remains inside of the stoma 3.

In detail, the tubular element 2 has a circular section. Alternative embodiments cannot however be ruled out in which the tubular element 2 has a square or polygonal cross section.

Figure 2:
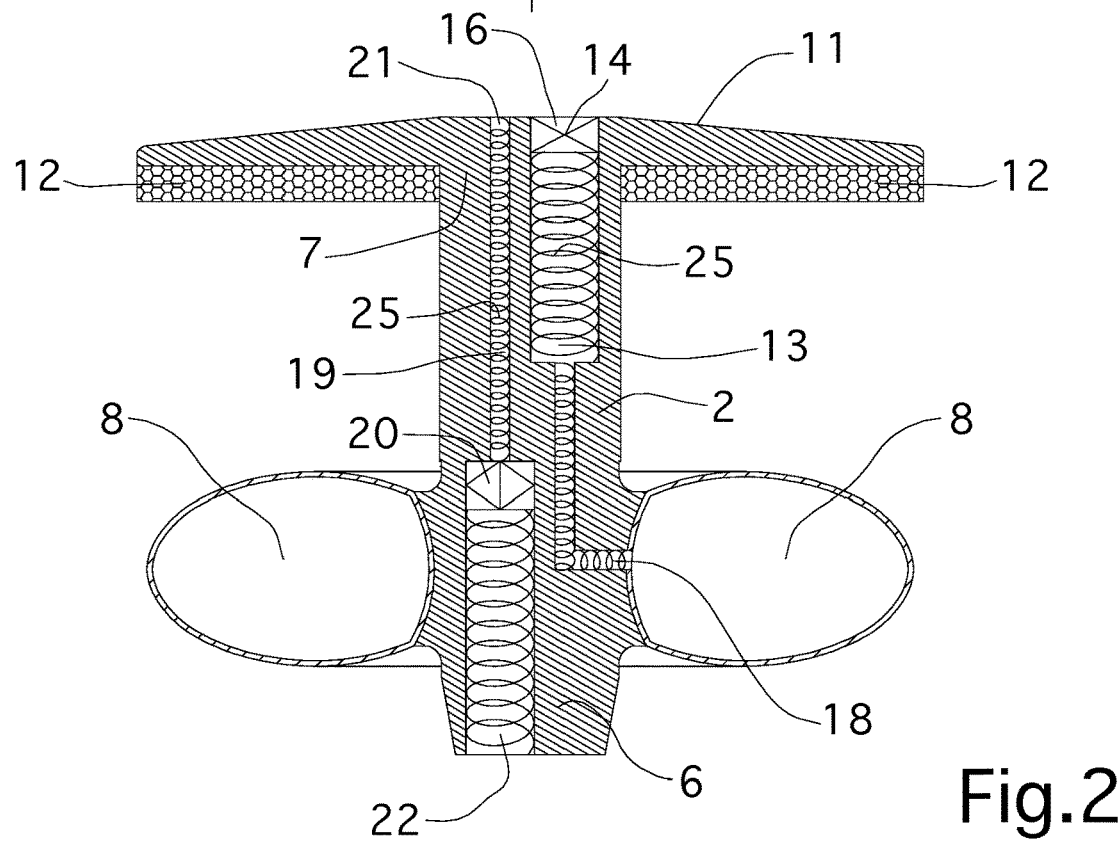
FIG. 2 is a sectional view of the prosthesis of FIG. 1.
Figure 3:
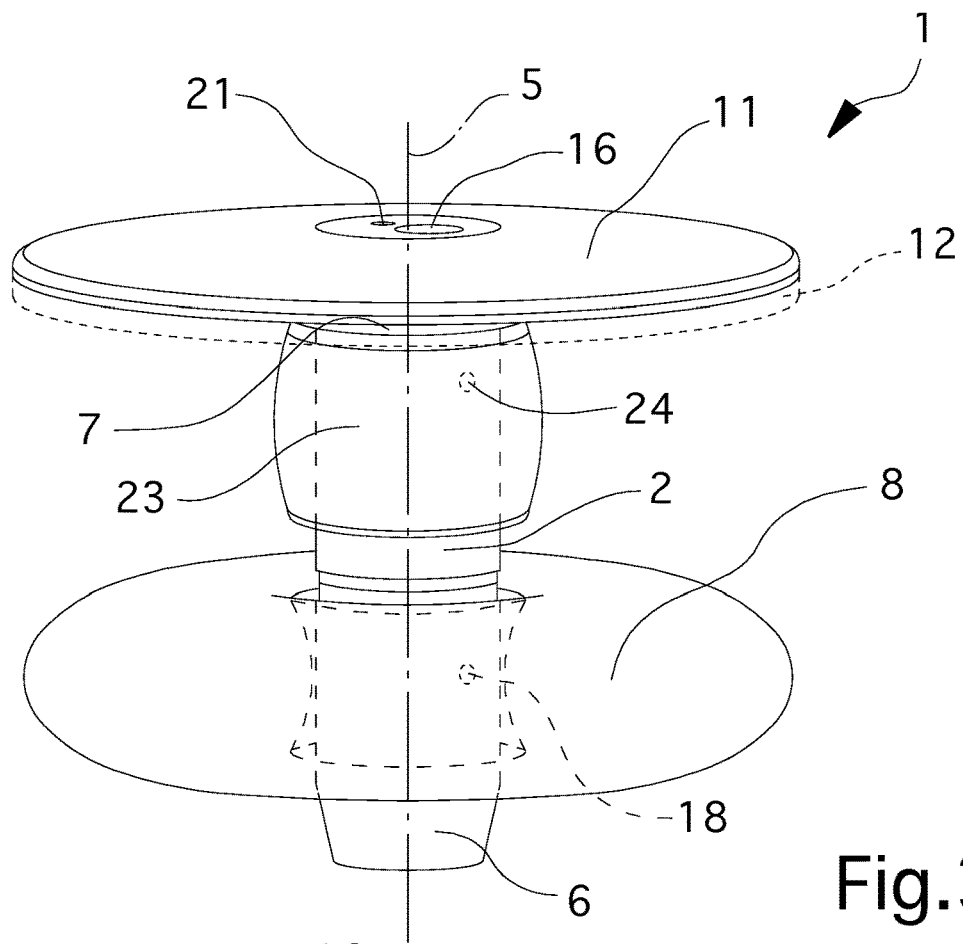
FIG. 3 is a front view of the prosthesis according to the invention in a second embodiment.
Figure 4:
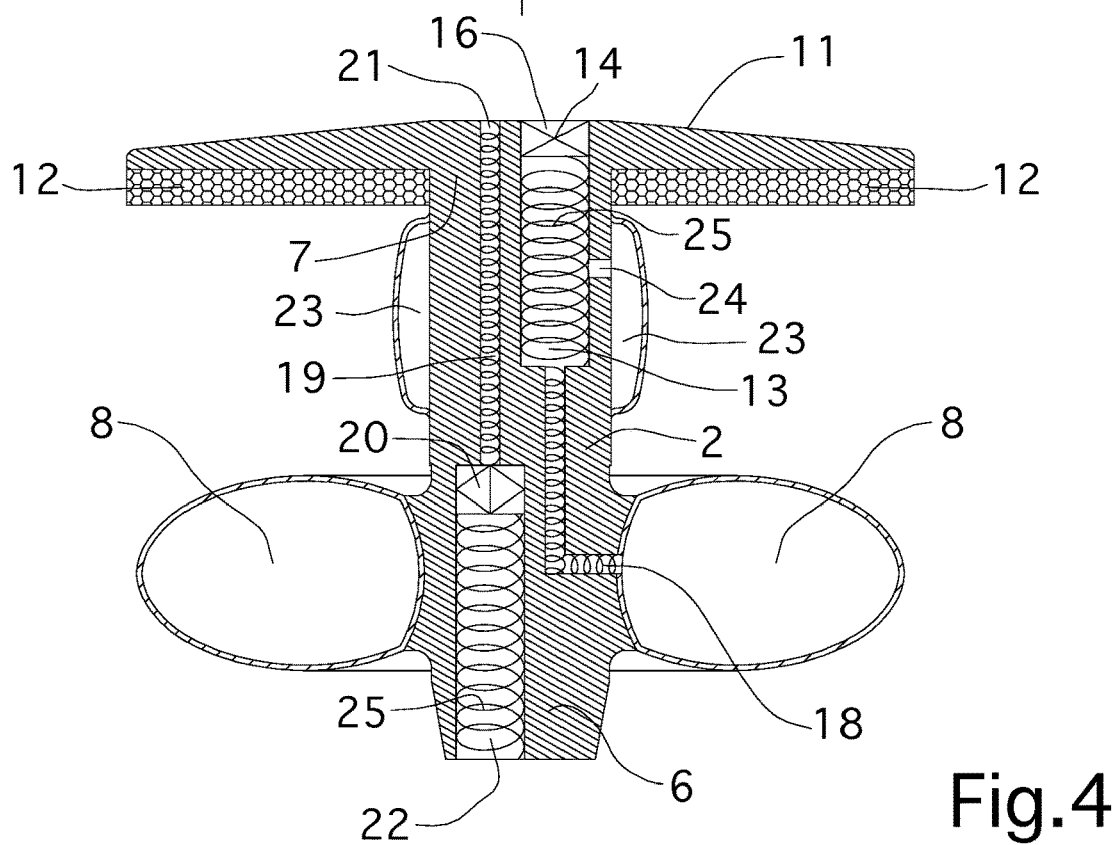
FIG. 4 is a sectional view of the prosthesis of FIG. 3.

In a first embodiment shown in FIGS. 1 and 2, the prosthesis 1 comprises first obstruction means 8 to obstruct at least one area of the stoma 3.

Figure 5:
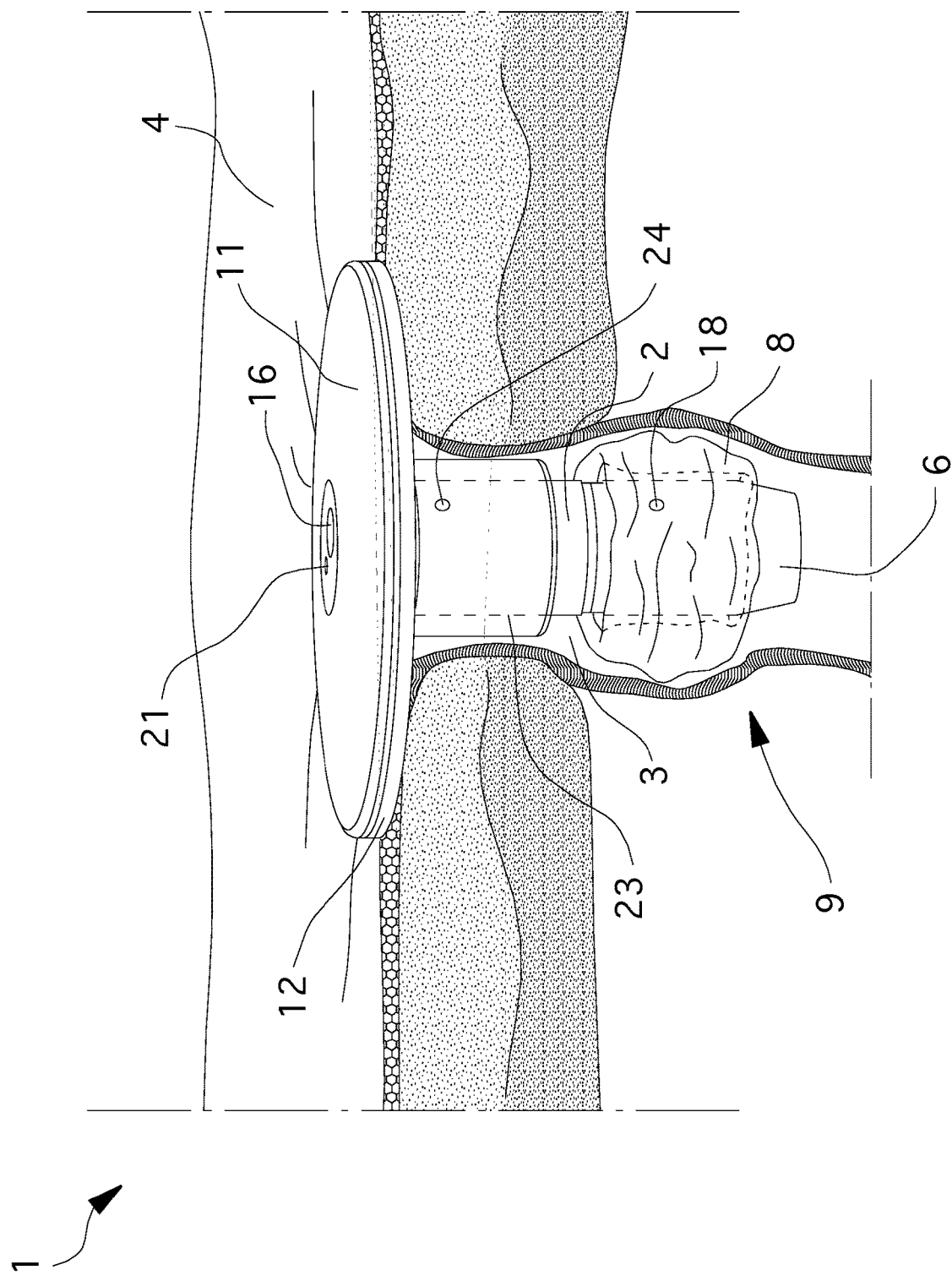
FIG. 5 is a schematic representation of the prosthesis of FIG. 3 in a first operating mode.

The first obstruction means 8 are associated with the first end 6 of the tubular element 2 and are movable between a restricted configuration 9 (in FIG. 5), and an enlarged configuration (in FIG. 6), to allow the insertion/extraction respectively of the tubular element into/from the stoma 3 and to prevent leakage of feces from the stoma itself.

The prosthesis 1 comprises an external retaining element 11 associated with the second end 7 of the tubular element 2 opposite to the first end 6 and adapted to cooperate with a portion of the abdominal wall 4 of the patient.

The retaining element 11 is of the type of a flange element abutting against the abdominal wall 4.

Advantageously, the retaining element 11 is coaxial to the tubular element 2. According to the invention, at least one of the tubular element 2 and the retaining element 11 is made at least partially of a flexible material.

Preferably, at least one of the tubular element 2 and the retaining element 11 is made of a flexible polymeric material of the type of rubber or the like.

It is useful to point out that in the present discussion by the term "flexible material" is meant a material able to deform elastically as a result of external stresses, such as e.g. abdomen flexions or particular positions taken by the patient.

With reference to a preferred embodiment, the tubular element 2 and the flange element 11 are made of a flexible material.

Preferably, the tubular element 2 and the flange element 11 are made of silicone-based polymeric mixtures.

Advantageously, the tubular element 2 and the flange element 11 are made in a single monolithic body.

Specifically, the tubular element 2 and the flange element 11, in practice, are made integral in a single body by means of, e.g., a manufacturing process by injection molding.

With reference to the particular embodiment shown in the figures, the prosthesis 1 comprises a yielding element 12 arranged along the tubular element 2 in the proximity of the flange element 11.

In the present case, the yielding element 12 is between the portion of the abdominal wall 4 of the patient and the flange element 11.

The prosthesis 1 comprises a first through duct 13 made on the tubular element 2 communicating with the first obstruction means 8.

The tubular element 2 has valve means 14 connectable to forced introduction/extraction means 15 of a fluid into/from the first obstruction means 8.

Furthermore, the valve means 14 comprise at least one two-way valve adapted to ensure the maintenance of pressurized air inside of the first obstruction means 8.

The first through duct 13 comprises a first communication hole 18 with the first obstruction means 8.

The first communication hole 18 is adapted to allow the entry/extraction of air from the first obstruction means 8, causing the passage from the restricted configuration 9 to the enlarged configuration 10.

The first duct 13 is connectable to the introduction/extraction means 15 by means of a first hole 16 made on the retaining element 11, i.e. on the flange.

The introduction/extraction means 15 may be of the type of a disposable syringe, having a spout 17 insertable inside of the first hole 16 for the introduction of the fluid inside of the first through duct 13.

In this regard it should be noticed that by the term "fluid" is meant any substance or mixture of substances which deforms indefinitely when subjected to a shear stress and, irrespective of the amount of the latter, with reference to a state of matter including substances in either gaseous or liquid state.

Specifically, in a preferred embodiment, the fluid used for the passage between the restricted configuration 9 (in FIG. 5) and the enlarged configuration 10 (in FIG. 6), is air.

The prosthesis 1 comprises a second duct 19 made on the tubular element 2, communicating with the inside of the stoma 3 and having filtering means 20 for the outflow of gases from the stoma itself.

As is visible in the figures, the second duct 19 extends longitudinally from the second end 7 to the first end 6.

The second duct 19 has a second hole 21 made on the retaining element 11, i.e. on the flange element, and an evacuation hole 22 made on the first end 6. Advantageously, the retaining element 11, that is the flange element, has the two through holes 16, 21 arranged at the first duct 13 and the second duct 19. Preferably, the filtering means 20 are of the type of an active carbon filter placed inside of a non-toxic rubber cartridge.

The prosthesis 1 comprises second obstruction means 23 arranged along the tubular element 2 and movable between a respective restricted configuration 9 (in FIG. 5), and a respective enlarged configuration 10 (in FIG. 6), to allow the insertion/extraction into/from the stoma 3 respectively, and to prevent feces from coming out of the stoma itself.

In detail, the second obstruction means 23 are adapted to vary the diameter of the tubular element 2 based on the diameter of the stoma 3, thus ensuring the substantially sealing obstruction of the stoma itself.

Preferably, the second obstruction means 23 are arranged in the proximity of the flange element 11.

Specifically, the second obstruction means 23 are in the proximity of the yielding element 12.

Preferably, the first obstruction means 8 and the second obstruction means 23 are coaxial to one another.

Advantageously, the first obstruction means 8 and/or the second obstruction means 23 are of the type of an inflatable balloon.

In the particular embodiment shown in FIGS. 3, 4, 5 and 6, both the first obstruction means 8 and the second obstruction means 23 are of the type of an inflatable balloon.

Figure 6:
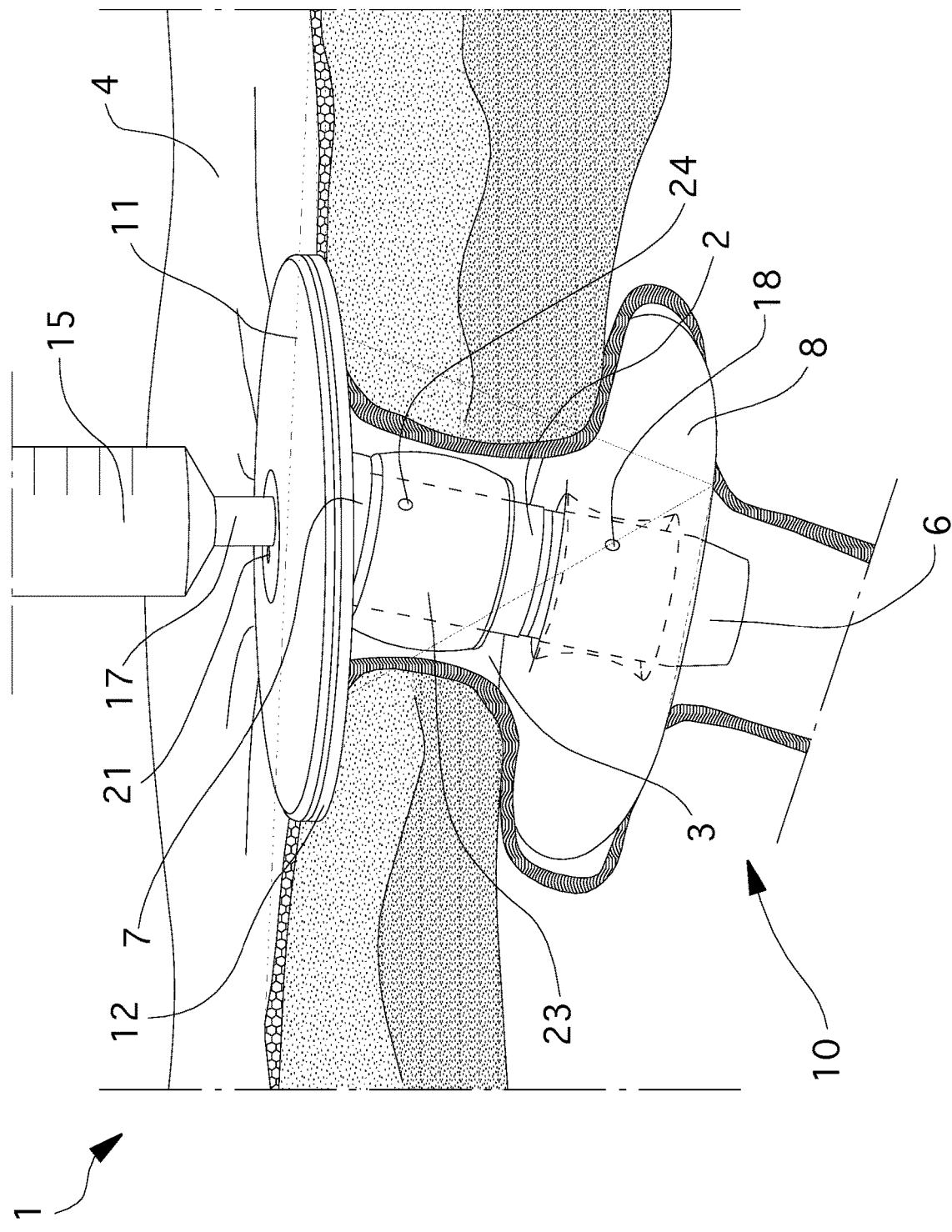
FIG. 6 is a schematic representation of the prosthesis of FIG. 3 in a second operating mode.

These inflatable balloons 8, 23 are arranged externally to the tubular element 2 and are substantially deflated in the restricted configuration 9 (in FIG. 5), and inflated in the enlarged configuration 10 (in FIG. 6).

Furthermore, the first through duct 13 comprises a second communication hole 24 with the second obstruction means 23 for the introduction/extraction of the fluid into/from the second obstruction means themselves.

In an alternative embodiment, not shown in the figures, the second obstruction means 23 are in communication with a third through duct made on the tubular element 2 and associable with the introduction/extraction means 15 of the fluid into/from the second obstruction means themselves.

In detail, the flange element 11 comprises a third through hole arranged at the third through duct and used for the passage of the fluid.

Similarly to the second duct 19, also the third through duct may have valve means 14, the type of a two-way valve, adapted to ensure the maintenance of pressurized air inside of the second obstruction means 23.

The prosthesis 1 comprises stiffening means 25 associated with at least one of the ducts 13, 19.

Advantageously, the stiffening means 25 are wound in a helix and extend at least partially inside of the ducts 13, 19.

In a preferred embodiment, the stiffening means 25 extend internally to the ducts 13, 19.

In detail, the stiffening means 25 are made of an elastomeric material of predefined hardness. Preferably, the aforesaid stiffening means 25 are made of a metallic material.

The presence of the stiffening means 25 is intended to prevent crushing of the ducts 13, 19 as a result of the movements of the tubular element 2.

For example, in case of particular positions taken by the patient such as twisting and/or bending of the abdominal wall 4, the tubular element 2, in turn, is subject to twisting and/or bending due to its peculiar properties of flexibility and adaptability. In such a situation, the action of the stiffening means 25 allows to maintain unchanged the section of the ducts 13, 19 also as a result of the above twisting and/or bending, without affecting the flexibility and overall adaptability of the tubular element 2.

The operation of the present invention is as follows.

An enterostomy patient inserts the prosthesis 1 inside of the stoma 3.

The first obstruction means 8 and the second obstruction means 23 are in the restricted configuration 9 (in FIG. 5), that is, they have their respective balloons deflated.

The prosthesis 1 is positioned by placing the yielding element 12 in contact with the abdominal wall 4.

After positioning the prosthesis 1, the patient provides for the inflation of the balloons 8, 23 by positioning the spout 17 of the disposable syringe 15 inside of the first hole 16.

More particularly, the balloons 8, 23 are brought to their respective enlarged configurations 10 (in FIG. 6) by blowing air through the first duct 13. This way the balloons 8, 23 inflate and, by widening, they occupy the whole section of the stoma 3.

As described above, the inflation of the balloons 8, 23 can be simultaneous or independent to one another depending on the fact that they have only the first inflation/deflation duct 13 for both balloons 8, 23 or two separate inflation/deflation ducts, respectively, namely the tubular element 2 has a third duct.

The balloons 8, 23 are deformable and when they are in the enlarged configurations they conform therefore to the inner walls of the stoma 3.

In fact, the first obstruction means 8 ensure the locking of the prosthesis 1 inside of the stoma 3, and the second obstruction means 23 allow to vary the diameter of the tubular element 2 according to the specific size of the stoma 3, i.e. substantially sealing it.

Taking into consideration the need to empty the intestinal contents outside, the patient deflates the obstruction means 8, 23, by inserting the spout 17 inside of the first hole 16 and by extracting the air out of the obstruction means themselves.

The obstruction means 8, 23 are in the restricted configuration 9 (in FIG. 5), and, therefore, the prosthesis 1 is extracted from the stoma 3 to allow the discharge of intestinal contents to the outside.

It has in practice been found that the described invention achieves the intended objects.

In particular, it is underlined that the particular expedient to provide for the presence of flexible materials allows for the realization of a prosthesis adaptable to any position taken by the patient.

To this is added that the fact of using elastomeric materials allows obtaining a prosthesis the shape of which is adaptable to the needs of patients and is made through constructive techniques such as injection molding which allow for a considerable reduction of the production costs of the prosthesis.

The invention claimed is:

1. A prosthesis for enterostomy patients, comprising:
   at least a tubular element of elongated shape and insertable substantially to size inside of a stoma made on the abdominal wall of a patient;
   at least first obstruction means to obstruct at least one area of the stoma, associated with a first end of said at least a tubular element and movable between a restricted configuration and an enlarged configuration to allow an insertion/extraction into/from said stoma respectively, and to prevent leakage of feces from the stoma;
   at least a first through duct made on said at least a tubular element, communicating with said at least first obstruction means and having valve means connectable to forced introduction/extraction means for conduction of a fluid into/from said at least first obstruction means;
   at least a second through duct made on said at least a tubular element, communicating with the inside of the stoma and having filtering means for an outflow of gases from the stoma; and
   at least an external retaining element associated with a second end of said at least a tubular element opposite to said first end and able to cooperate with at least one portion of the abdominal wall and having at least one through hole arranged at said at least a first duct and said at least a second duct;
   wherein at least one of said at least a tubular element and said at least an external retaining element is made at least partially of a flexible material;
   wherein said at least a first through duct comprises a first communication hole with said at least first obstruction means, and a second communication hole with a second obstruction means for the introduction/extraction of said fluid into/from said at least first obstruction means and said second obstruction means, respectively.

2. The prosthesis according to claim 1, wherein said second obstruction means is arranged along said at least a tubular element and movable between a respective restricted configuration and a respective enlarged configuration to allow the insertion/extraction into/from said stoma respectively, and to prevent feces from coming out of the stoma.

3. The prosthesis according to claim 2, wherein said prosthesis further comprises at least a third through duct made on said at least a tubular element, communicating with said second obstruction means and connectable to said forced introduction/extraction means for conduction of said fluid into/from said second obstruction means.

4. The prosthesis according to claim 2, wherein said at least first obstruction means and/or said second obstruction means are an inflatable balloon.

5. The prosthesis according claim 1, wherein said at least a tubular element and said retaining element are made of a flexible material.

6. The prosthesis according to claim 1, wherein said at least a tubular element and said retaining element are made in a single monolithic body.

7. The prosthesis according to claim 1, wherein said prosthesis comprises stiffening means associated with at least one of said ducts.

8. The prosthesis according to claim 7, wherein said stiffening means are wound in a helix and extend at least partially inside of said first through duct and said second through duct.

9. The prosthesis according to claim 7, wherein said stiffening means are made of an elastomeric material of predefined hardness.

10. The prosthesis according to claim 7, wherein said stiffening means are made of a metallic material.

* * * * *